United States Patent [19]

Weissenfluh et al.

[11] Patent Number: 5,775,905
[45] Date of Patent: Jul. 7, 1998

[54] CUP AS A CARRIER OF PASTES FOR DENTAL HYGIENIC

[75] Inventors: Beat A.v. Weissenfluh, Gentilino; Gianni Baffelli, Tesserete, both of Switzerland

[73] Assignee: Hawe Neos Dental Dr. H.v. Weissenfluh AG, Bioggio, Switzerland

[21] Appl. No.: 840,131

[22] Filed: Apr. 11, 1997

[30] Foreign Application Priority Data

Apr. 11, 1996 [CH] Switzerland .................. 0914/96

[51] Int. Cl.$^6$ ........................................ A61C 3/06
[52] U.S. Cl. .................................. 433/166; 433/125
[58] Field of Search .............................. 433/125, 166, 433/126

[56] References Cited

U.S. PATENT DOCUMENTS

| | | | |
|---|---|---|---|
| 899,626 | 9/1908 | Schultz | 433/166 |
| 3,727,315 | 4/1973 | Spinello . | |
| 4,259,071 | 3/1981 | Warden et al. | 433/166 |
| 4,854,870 | 8/1989 | Kofod | 433/166 |
| 5,360,339 | 11/1994 | Rosenberg . | |
| 5,380,202 | 1/1995 | Brahler . | |
| 5,599,333 | 2/1997 | Atkinson . | |

FOREIGN PATENT DOCUMENTS

| | | |
|---|---|---|
| 0372960 | 6/1990 | European Pat. Off. . |
| 2090970 | 1/1972 | France . |

*Primary Examiner*—Nicholas D. Lucchesi
*Attorney, Agent, or Firm*—Foley & Lardner

[57] ABSTRACT

The cup to be used as a paste carrier for dental hygienic consists of a rubber elastic material and can be driven for rotation by a hand piece. The cup comprises a paste receiving part, the inner side enlarging towards its open edge as well as the outer side of the cup enlarging towards its open edge comprising spiraled ribs which are running in the opposite direction to the rotational direction of the hand piece. The structure on the inner side of the paste receiving part allows a continuous supply of paste and a cooling of the cup, and the structure of the outer side of the cup prevents a bale formation of the mucous and guarantees an effective cooling of the cup.

4 Claims, 2 Drawing Sheets

CUP AS A CARRIER OF PASTES FOR DENTAL HYGIENIC

FIELD OF THE INVENTION

The present invention refers to a cup for carrying cleaning paste in dental hygienic, the cup consisting of a rubber elastic material and being drivable by a hand piece, the cup comprising a paste receiving portion, the inner side of this paste receiving portion that enlarges towards its open edge and the outer side that also enlarges towards its open edge being structured.

BACKGROUND OF THE INVENTION

Such a cup, sometimes designed as a "dental prophy cup", is known from the U.S. Pat. No. 5,380,202. The cup comprises outer longitudinal ribs and inner longitudinal ribs that serve exclusively for a better teeth cleaning.

In modern dentistry, the teeth of the patients are cleaned from films adhering thereto, and this is done for aesthetic as well as dental prophylactic reasons. The cleaning is effected by paste carrier, so-called prophy-cups, which are filled with an abrasive paste, the so-called prophy-paste. These prophy-cups are made to rotate, generally in clockwise direction, are brought into contact with the teeth, and the paste-cup system exerts its cleaning effect under varying pressure. Instead of cups, a brush may be used or a powder jet device, but these devices have not found widespread use.

A plurality of cups can be found on the market which may also comprise a structure on the outer or inner walls. In general these cups are made of silicon rubber, for example as disclosed in U.S. Pat. No. 3,599,333. The U.S. Pat. No. 3,727,315 discloses a dental prophylaxis apparatus with a cup-shaped cleaning member with inclined grooves on the outer surface which, together with a wiper finger, have the function to direct the paste on the outer surface of the cup toward the working end of the cup. From the EP-A-372, 960it is known to provide the inside of the cup with a plurality of ribs positioned at an angle to the axis for retaining the paste. These and other known cups have considerable disadvantages: the tooth will warm up proportionally to the pressure and the time of treatment. This warming up may be disagreeable or even painful to the patient. The rotating action has the tendency of collecting and dragging along the stringy saliva. A mucous bale is thus formed on the outer side of the cup together with the paste. When a critical size is reached, the mucous bale begins to splash around, and the so-called "splattering" occurs.

This splattering causes serious hygienic problems due to bacterial contamination and may infect the treating person, the treated patient and the environment. Therefore, the treatment with known cups requires frequent interruptions for removing the mucous bales and thus to reduce splattering. However, relatively large portions of the paste remain thus unemployed or are without effect since they are collected in the mucous bales and disposed of. This mucous bale formation and the subsequent splattering are generally considered as being the most important drawback of the known cups and their application.

The form of the current cups comprises a cavity on the inner side which may receive and then deliver a certain amount of paste for application. Most known cups function in that they deliver, when beginning the application by rotation, a large amount of paste until only the dead corner of the cavity is filled with paste and remains filled. This results in the fact that these cups allow the cleaning of one tooth only or two teeth at the most until the supply of paste is exhausted and the treatment must be interrupted for a refill. This is a further inefficient and undesired discontinuity of the use of such cups.

The cup according to U.S. Pat. No. 5,360,339 has a structure on its inner side in order to achieve a better paste supply and distribution. To this end, it comprises lengthwise and traverse channels having chamfered edges. Although an improvement over other cups having no similar structure appears to be possible, the uniform distribution of the paste still remains unsatisfactory, and the problem of the strong warming up of the teeth still subsists.

SUMMARY OF THE INVENTION

Starting from this prior art, it is an object of the present invention to provide a paste carrying cup which effectively prevents warming up of the tooth even on prolonged treatment, and which guarantees also a continuous paste supply and prevents the forming of mucous bales and its subsequent bursting.

This object is attained by the cup of the invention which comprises, as well on its outer surface and as on its inner surface, spiraled ribs which are running in the opposite direction to the rotational direction of the hand piece. In further improvements, the ribs may be arranged according to an Archimedean screw, and lamellae which are separated by interruptions may be disposed beneath and parallel to the open inner edge of the cup. Preferably, the cup is made of a thermoplastic elastomer.

Further features, advantages and particulars of the invention will become evident from the following description of an embodiment thereof which is shown in the drawing.

DESCRIPTION OF THE PREFERRED EMBODIMENTS OF THE INVENTION

Figure 1:
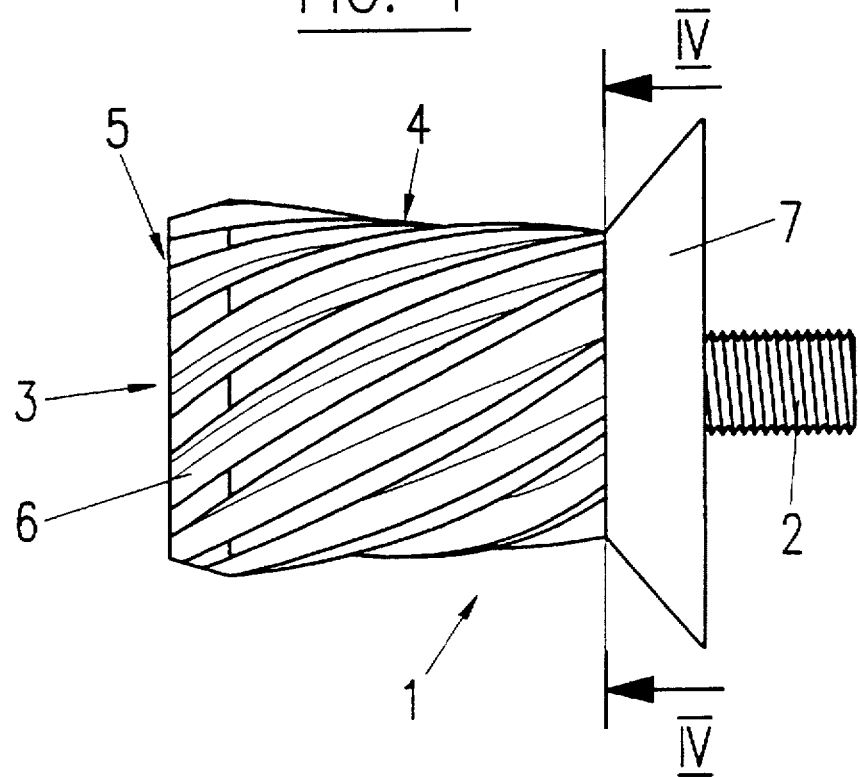
FIG. 1 shows a side elevation of the cup according to the invention.
Figure 2:
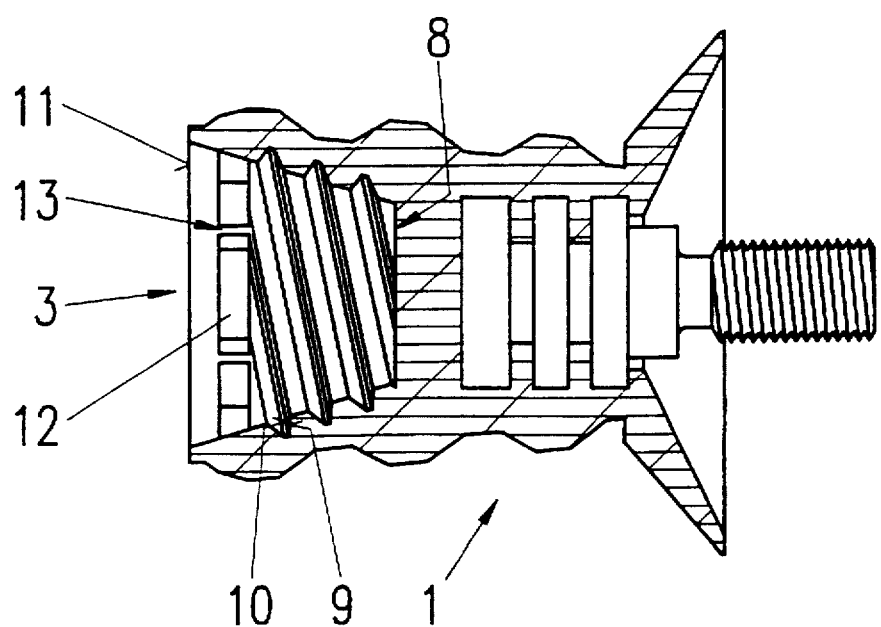
FIG. 2 is a longitudinally sectioned view of the cup of FIG. 1.
Figure 3:
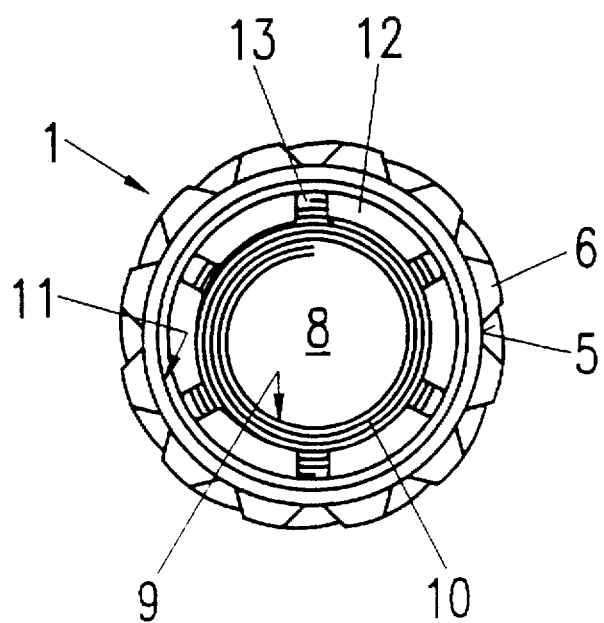
FIG. 3 shows a frontal view, as from the left in FIG. 1, of the cup of FIG. 1.
Figure 4:
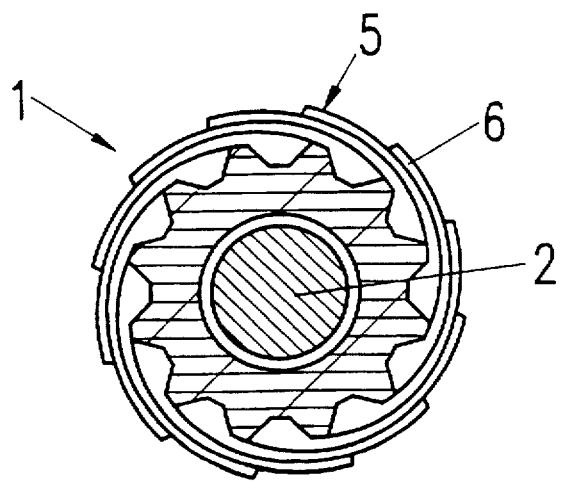
FIG. 4 shows a sectional view according to line IV—IV in FIG. 1.

The cup 1 consists substantially of a fastening portion having a threaded stem 2, and a paste receiving portion 3. The cup can be fastened by means of its threaded stem 2 to a hand piece (not shown) which drives the cup generally in clockwise direction. The threaded stem 2 is manufactured from a metal. The remaining parts of the cup are made of a rubber elastic material. A plurality of such rubber elastic materials is known, for example natural rubber or synthetic rubber. Different synthetic rubbers may be contemplated according to the desired elastic property and the nature of the surface. Since the heating is a consequence of the sliding friction of the cup on the tooth, it is advantageous to use materials having a reduced sliding friction. Such substances are for example halogenated polymers, one of them being known under the trade name "TEFLON", or thermoplastic elastomers. It is important that the coefficient of friction on the teeth should be relatively small.

The cup must not necessarily be provided with a threaded stem; instead, other, known fastening devices could be used such as a snap-on or otherwise locking connection to the driving means.

The outer side 4 of the cup is essentially conically enlarged towards the open outer edge 5 and comprises spirally ribs 6 running counterclockwise, these ribs being arranged according to the principle of the Archimedean screw. When the cup is rotated clockwise, this counterclockwise, relatively high pitch of the ribs shovels the paste and the saliva continuously toward the cup edge 5 that represents the very site of action of the paste. Paste loss by splattering is therefore prevented, and there are no longer interruptions of the work due to mucous bales.

The paste receiving part 3 has a cavity which, starting from the bottom 8, enlarges towards the exterior, and the inner surface 9 also comprises spiraled ribs 10 which are counterclockwise arranged as are the outer ribs 6. The ribs 10 are also disposed according to the principle of the Archimedean screw.

It will be evident that, when the cup would be driven in counterclockwise direction, the ribs should be spiraled in clockwise direction, i.e. always against the rotational direction of the cup driven by the hand piece. The outer side of the cup is closed towards the threaded stem by a collar 7 whose circumference increases toward the threaded stem, i.e. the collar is a conical one.

Somewhat below the open inner edge 11, lip-like lamellae 12 are disposed substantially parallel to that inner edge 11. These lamellae, for example a number of six, act like a spear valve and seal the inner space of the cup and 5 the paste receptacle against the exterior. However, a complete sealing is not desired but paste should be continuously supplied towards the cup edge. This is achieved in disposing interruptions 13 between the lamellae, for example six interruptions having a width of 0.5 mm each. In this manner, the paste supply becomes continuous, and the consumption of paste is strongly reduced. The previously known and undesired paste loss in the dead corner of the interior of the cup is eliminated. The new inner structure has a two-fold function, namely the continuous paste supply and the carrying-off of heat. The outer ribs further supply cooling air whose amount is increased by their shovel-like spiraled configuration.

What is claimed is:

1. A cup drivable by a hand piece for carrying a cleaning paste in dental hygienic, comprising:

a paste receiving portion having an inner side that enlarges toward an open edge of the paste receiving portion and an outer side that enlarges toward said open edge;

wherein said inner side and outer side of the paste receiving portion include spiraled ribs which run in a direction opposite to a rotational direction of the hand piece.

2. The cup of claim 1, wherein the spiraled ribs are disposed according to the principle of an Archimedean screw.

3. The cup of claim 1, wherein lamellae are disposed below the inner edge and substantially parallel to the inner edge, the lamellae being separated by interruptions.

4. The cup of claim 1, wherein the paste receiving portion is comprised of a thermoplastic elastomer.

* * * * *